(12) United States Patent
Barfuss et al.

(10) Patent No.: US 7,508,392 B2
(45) Date of Patent: Mar. 24, 2009

(54) METHOD FOR EXPANDING THE DISPLAY OF A VOLUME IMAGE OF AN OBJECT REGION

(75) Inventors: Helmut Barfuss, Erlangen (DE); Karl Barth, Höchstadt (DE); Gerd Wessels, Effelrich (DE)

(73) Assignee: Siemens Aktiengesellschaft, Munich (DE)

( * ) Notice: Subject to any disclaimer, the term of this patent is extended or adjusted under 35 U.S.C. 154(b) by 173 days.

(21) Appl. No.: 11/438,030

(22) Filed: May 19, 2006

(65) Prior Publication Data

US 2006/0267977 A1 Nov. 30, 2006

(30) Foreign Application Priority Data

May 19, 2005 (DE) .................. 10 2005 023 195

(51) Int. Cl.
*G06T 15/00* (2006.01)
(52) U.S. Cl. .................. 345/428; 345/419; 345/629
(58) Field of Classification Search ......... 345/418–420, 345/426, 428, 629–630
See application file for complete search history.

(56) References Cited

U.S. PATENT DOCUMENTS

| | | | | |
|---|---|---|---|---|
| 5,087,345 | A | * | 2/1992 | Kashiwada et al. ......... 204/295 |
| 5,987,345 | A | | 11/1999 | Engelmann et al. |
| 6,078,349 | A | | 6/2000 | Molloy ........................ 348/15 |
| 6,630,937 | B2 | | 10/2003 | Kallergi et al. |
| 6,909,436 | B1 | * | 6/2005 | Pianykh et al. .............. 345/619 |
| 7,191,110 | B1 | | 3/2007 | Charbel et al. |

(Continued)

FOREIGN PATENT DOCUMENTS

DE 101 51 438 1/2003

(Continued)

OTHER PUBLICATIONS

Bajura et al. Merging Virtual Objects with the Real World: Seeing Ultrasound Imagery within the Patient; ACM—Computer Graphics, Jul. 1992, pp. 203-210.*

(Continued)

*Primary Examiner*—Phu K Nguyen
(74) *Attorney, Agent, or Firm*—Schiff Hardin LLP

(57) ABSTRACT

In a method for expanding the display of a volume image of an object region, in particular in medical applications, in which at least one first image data set of a larger object region is made available, at least one second image data set of a smaller object region is acquired, the smaller object region lying within the larger object region, and the first 3D image data set is brought into registration with the second 3D image data set. A synthesized 3D image data set is generated from the first and second 3D image data sets and visualized in a display. The first 3D image data in the first 3D image data set represent the smaller object region, if necessary after a suitable adaptation of the first and/or of the second 3D image data set, are replaced by second 3D image data of the second 3D image data set with identical scaling and alignment of the image data sets. An overview of the larger object region thus is possible, and the smaller object region of interest the image can be represented with up-to-date data as well as a higher resolution and/or a higher contrast.

16 Claims, 2 Drawing Sheets

U.S. PATENT DOCUMENTS 7,311,705 B2 12/2007 Sra
2003/0181809 A1 9/2003 Hall et al. .................. 600/427

FOREIGN PATENT DOCUMENTS

EP 1 056 049 11/2000

OTHER PUBLICATIONS

Hauser et al., Two-level Volume Rendering—fusing MIP and DVR, IEEE—Visualization, 2000, pp. 211-218.*

Hu et al., Volumetric Rendering of Multimodality, Multivariable Medical Imaging Data, Symposium on Volume Visualization, 1989, pp. 45-52.*

"Super-Resolution Imaging: Use of Zoom as a Cue," Joshi et al, Image and Vision Computing, vol. 22 (2004) pp. 1185-1196.

"Visualization and Interaction Techniques for the Exploration of Vascular Structures," Hahn et al., Center for Medical Diagnostic System and Visualization, Bremen Germany (2004), pp. 395-402.

"Multi-Modality Gaze-Contingent Displays for Image Fusion," Nikolov et al., Proc. of the 5th Int. Conf. on Information Fusion, vol. 2 (2002) pp. 1213-1220.

* cited by examiner

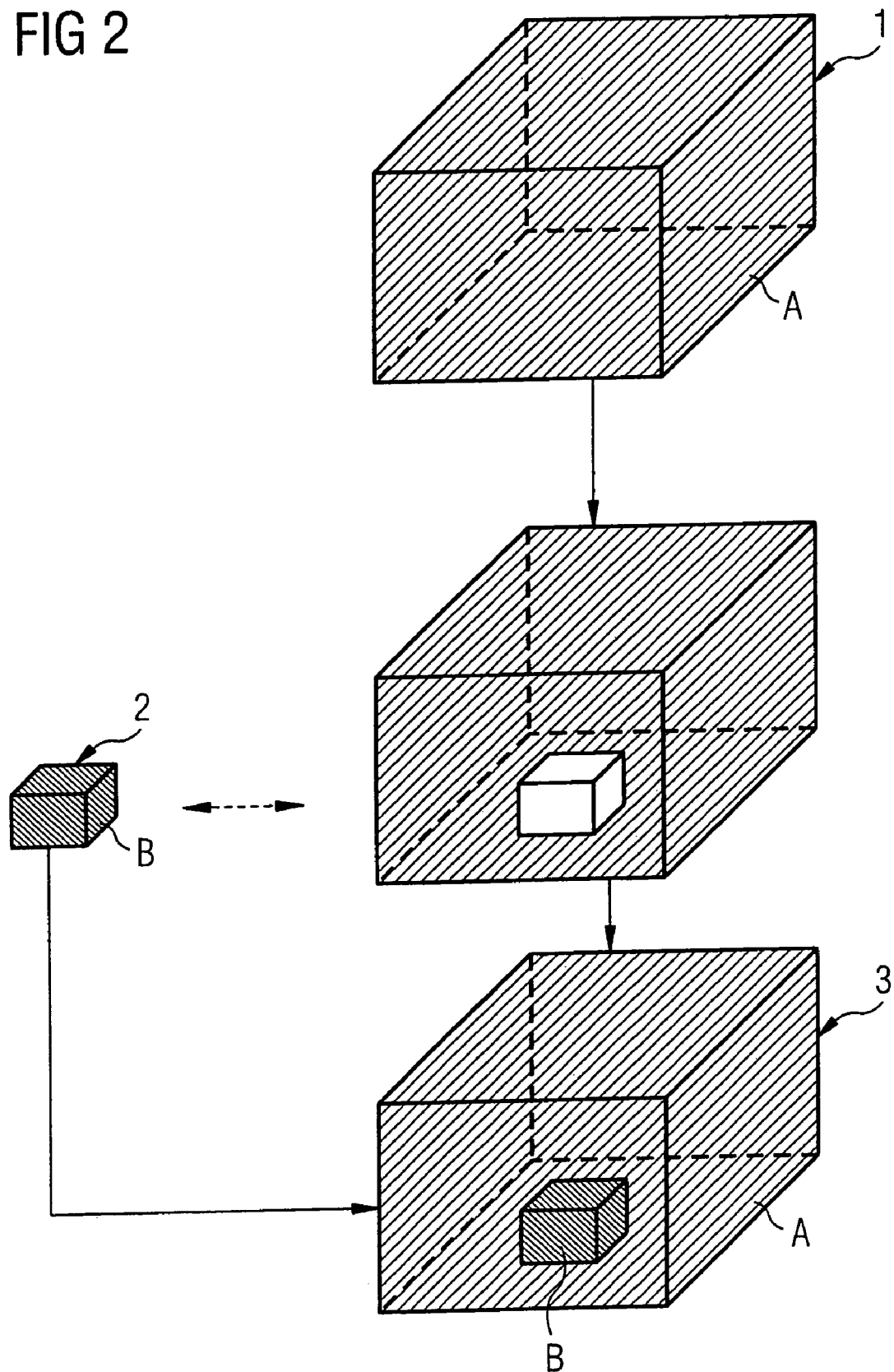

METHOD FOR EXPANDING THE DISPLAY OF A VOLUME IMAGE OF AN OBJECT REGION

BACKGROUND OF THE INVENTION

1. Field of the Invention

The present invention relates to a method for expansion of the display of a volume image of an object region, of the type wherein a first image data set of a larger object region is made available, a second image data set of a smaller object region is acquired, the smaller object region lying within the larger object region, and the image data sets are displayed in combination.

2. Description of the Prior Art

In surgery, compact imaging systems such as mobile x-ray devices, ultrasound devices or endoscope/laparoscope are often used. These modalities, however, offer only a limited field of view for visualization. For surgeons, it is desirable to be able to see the local environment of the treatment region in a larger field of view.

Various options are known in whereby at a time interval prior to surgery, 3-D images of the body, e.g., by means of computed tomography or magnetic resonance tomography, are acquired in order to be able to visualize the local environment with these 3-D images during the surgery. For using pre-surgery images during the surgery, a current local representation of the treatment region appears on a primary monitor, the representation being acquired e.g. with the mobile imaging modality. On a secondary monitor an image superimposition or fusion takes place. The current local representation, e.g. an endoscopic view, is directly superimposed on the overall view from the pre-surgery image. Both views can be shown suitably transparent and in complementary colors. DE 102 10 646 A1 describes such a superimposition of the image data of a 3D imaging modality with the 2D fluoroscopic image of an examination region.

SUMMARY OF THE INVENTION

An object of the present invention is to provide a method for expanding the viewport of a volume image of an object region that offers advantages particularly in the case of using a mobile compact device for image acquisition.

This object is achieved in accordance with the invention by a method wherein at least one first 3D image data set of a larger object region is provided which preferably was recorded previously with an imaging tomographic modality. At least one second 3D image data set of a smaller object region is acquired, this region lying within the larger object region. The first and second 3D image data sets are brought into registration. The acquisition of the second 3D image data set preferably takes place with a mobile compact device that exhibits only a limited field of view for imaging. Such a compact device can be, for example, a mobile 3D x-ray C-arm device or an imaging ultrasound device suitable for 3D imaging. A synthesized 3D image data set is generated from the first and second 3D image data sets, in which the first 3D image data in the first 3D image data set representing the smaller object region, if necessary after a suitable interpolation for adaptation of the resolution, are replaced by second 3D image data of the second 3D image data set with identical scaling and alignment of the image data sets.

The synthesized 3D image data set is then visualized for the user in an image display.

Since generally the locally smaller second 3D image data set exhibits the higher resolution, for adaptation purposes interpolation of the first 3D image data set is preferred, in order to achieve a refined screening of the second 3D image data set. The voxel number of the second 3D image data set can be greater than the voxel number of the first 3D image data set.

Both the pre-operative volume image, for example a CT image, as well as the intra-operative volume image are obtained in a defined position and orientation relative to the object, so that registration of the respective 3D image data sets with each other is possible. Many of the devices that can be used, for example a CT device and a 3D C-arm device, are generally designed for this purpose. Both modalities cited as examples generate volume data sets that contain a dimensioning in accordance with the DICOM standard. On this basis it is possible in various ways to correctly correlate both data sets, thus the registration. For this purpose in the following three variants will be cited as examples.

In the first variant, a fixed allocation of cameras to a patient table takes place, with the patient being reproducibly fixed on the table, for example by a stereotactic frame or by means of bite fixation (for head exposures). Through this fixed allocation of the cameras to the patient table and the fixation of the patient to the patient table, registration is already guaranteed.

In a second variant, prior to acquiring the first 3D image data set, e.g. a CT image, contrast marks are put on the patient. These marks remain on the patient during the subsequent operation and are used again intra-operatively both for the following volume images as well as also for the surgical measures (mark-based registration). The marks are detectable in the 3D image data sets and thus can be used for the registration or correct allocation of the two 3D image data sets.

In a third variant, the registration of the two 3D image data sets is performed by distinctive structures (landmarks) in the acquired volume images. For this purpose identical structures are identified in the previously acquired overview image of the first 3D image data set and in the local high resolution volume image of the second 3D image data set. Subsequently, the required rotation and translation matrix is determined to bring about an identical superimposition of these structures in the image data sets (markless registration).

In the inventive method hence the currently recorded 3D image of the local object volume is integrated into the pre-operatively acquired image, with the advantages that the current status as well as, if necessary, a high resolution and a better contrast can be used, since the pre-operative image encompasses a greater object or volume region, but exhibits an older acquisition time as well as possibly a lower resolution and/or a lower contrast. Consequently the object or volume region that can be represented is expanded with the present method. Furthermore, with suitable generation of the second 3D image data set the registered smaller object region can be represented with an increased resolution and/or an increased contrast. This smaller object region will also be designated in a following as core region or core image, and the comprehensive total representation will be termed environment image.

In a preferred development of the present method the second 3D image data set is acquired with a higher resolution or a different characteristic (e.g., by using tracers or contrast media) than the first 3D image data set. For synthesizing, the first 3D image data set of the greater object region is adapted by means of interpolation of image data to the higher resolution of the second 3D image data of the second 3D image data set that is to be integrated. In a further embodiment, the second 3D image data set is also acquired with a higher image contrast than the first 3D image data set. This results in a locally better and more current detail representation in a restricted region of the combined image representation. The synthesis of the two images takes place on the basis of a correct location and position registration as well as, preferably, on the basis of a calibration during the recording of the second 3D image data sets, so that the two volumes can be joined together to precisely defined sizes.

The advantages of the present method are primarily achieved as a result of the fact that the second 3D image data is integrated by the substitution of the first 3D image data in the image display of the larger object region. For this purpose the smaller object region is removed (excised) from the first 3D image data set and replaced by the second 3D image data of the second 3D image data set. An image superimposition does not take place in this connection as is the case with known methods of the state of the art. Nevertheless, such an image superimposition can be provided as an additional option for the user.

The present invention is particularly suitable for mobile x-ray imaging, e.g., by means of a mobile 3D-capable C-arm device. Such a device can be very quickly brought from a standby position to the operating table, where the x-ray source and the x-ray detector can be optimally adjusted at any time by means of the coupling via the C-arm. In the further course of the surgery such a device often can remain on site, since patient access for the physician in the relatively small opening of the C-arm generally remains free. A disadvantage of using such a mobile x-ray device, however, is that, due to the required compactness and lower x-ray performance and detector geometry associated therewith, only a relatively small 2D image region (raw data) is registered with each projection.

The volume image (3D) reconstructed from many projections consequently also has only a small volume extent. Expanded body structures are cut off on the margins of the image representation. Precisely this disadvantage can be prevented with the present method by means of expanding the viewport.

In an embodiment of the present method a superimposition of all layers penetrated by radiation in central projection is not calculated from the first 3D image data, but instead a region within a particular depth region is determined and excised, the depth range encompassing the essential structures reproduced by the second 3D image set. In this embodiment use is made of the fact that the structures of interest in the second 3D image set often exhibit a smaller depth region of the object. Thus in this embodiment the data in the corresponding depth range are removed from the first 3D image data used for the 3D image representation of the first, larger object region, and into which the second 3D image data set is integrated. The first 3D image data of the environment image can be depth-coded (indexed) beforehand to facilitate the depth selection. By means of this depth coding the depth selection can take place especially quickly, for example supported by hardware and/or via a lookup table in which the coding of the various depth regions is allocated.

In another embodiment of the present method, the first 3D image data set can be preprocessed such that only those structures of the larger object region which are of interest for the user for a particular application are present, or at least are highlighted in the image representation. Thus the first 3D image data set can represent e.g., and exposure of the larger object region obtained by high contrast CT, in which case only the contrast medium-filled vessel structures are of interest. The possibility also exists to acquire several 3D image data sets of various parts of the larger object region in advance and then to combine them for reconstruction of the larger object region in order to obtain the first 3D image data sets.

In the inventive method it is of course also possible to integrate several second 3D image data sets of various small object regions into one suitable total representation with the provided first 3D image data sets. Also a switching between the display of various core regions can be provided. In a further embodiment various representations of the second 3D image data set, e.g., with variable contrast or after the application of filters for the emphasis of various structures in different color coding, can be combined with the representation of the larger object region. Here as well, a switching between the various representations is possible. Furthermore, a superimposition of the different representations of the core region can take place, wherein the transparency or brightness of the various superimposed representations can be modified by the user, preferably in a continuous manner.

The different embodiments of the method of course can be combined. Moreover, although embodiments of the inventive method are explained using imaging in the case of a medical application, they can also be used easily in non-medical applications for other objects.

The present invention also can be used for setting of the modality used for acquiring the second 3D image data set in order to be able to optimally focus the acquisition system or the optics thereof on the desired core region. For this purpose, prior to the acquisition of the second 3D image data set of the smaller object region, an image of the larger object region is generated from the first 3D image set and displayed to a user. The user then has the possibility of interactive definition of the smaller object region for the acquisition of the second 3D image data set, whereupon the data of the defined object region are entered into a control unit of the system used for acquisition of the second 3D image data set. For this purpose, a registration of the first 3D image data set with this imaging system must take place, e.g. via marks placed on the patient and a navigation device coupled to the imaging system with which these marks can be navigated to. In a further embodiment of this method variant, the image of the larger object region can be suitably enlarged, rotated 3-dimensionally and translated.

DESCRIPTION OF THE DRAWINGS

FIG. 2 schematically illustrates the generation of the synthesized 3D image data set in accordance with the invention.

DESCRIPTION OF THE PREFERRED EMBODIMENTS

Figure 1:
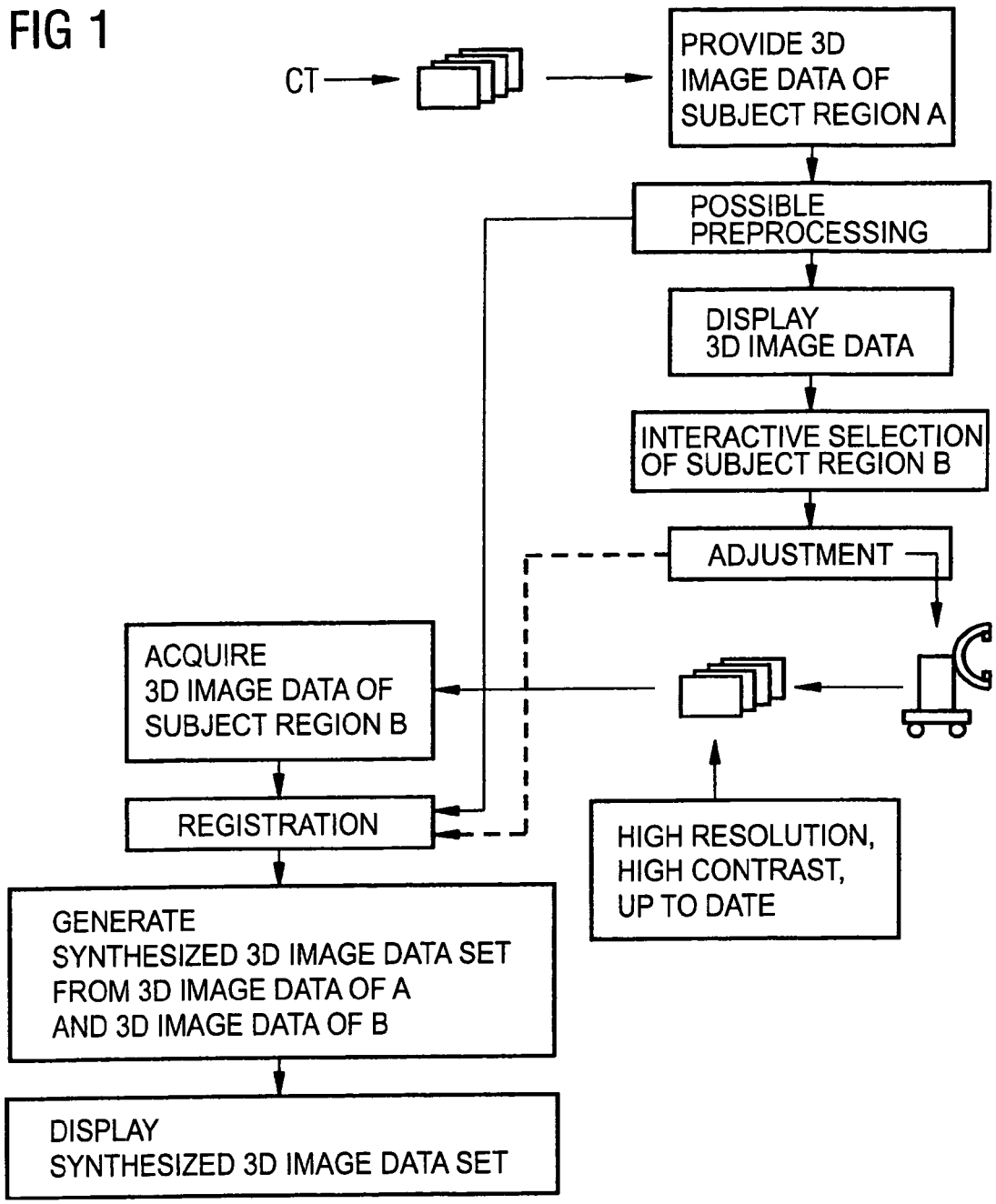
FIG. 1 schematically illustrates an embodiment of the method of the present method.

The present method will be described again in detail using the example of an operation, e.g., after a pelvic fracture, during which a 3D image of the treatment region is acquired and displayed with a mobile 3D C-arm device.

Currently many 3D image data sets are often used both for planning as well as for implementing a method procedure, the 3D image data sets being generated, e.g., from CT volume images prior to the operation. By means of the visualization of these 3D image data sets a complete, large-scale overview results of the total relevant body environment. In the case of surgery, however, the physician must for various reasons proceed based on a current imaging, for example, is obtained by means of imaging endoscopy, ultrasound or mobile 3D x-ray imaging. In the case of repeated imaging during the operation, the physician can also immediately track changes in this way. The current imaging is already necessary for safety, since changes in the anatomy of the patient could have occurred since the preliminary examination, e.g. due to the shifting of soft tissue structures. Furthermore, the current local imaging often can be generated with a higher image quality, since the image parameters can be set for higher resolution and specially optimized contrast.

In the present example, a mobile x-ray C-arm device is used as an imaging x-ray system during the operation. Such a device can be easily operated and provides acceptable access to the patient on the operating table. Above all a mobile x-ray C-arm device allows very high resolution imaging, since it is possible to scan only a small image region with high local frequency. In addition in the smaller region the dynamics and the contrast can be specifically optimized. Thus an optimum, current 3D image can be obtained with the local volume mapping.

Due to the compactness of such a mobile x-ray C-arm device however only a smaller image region is acquired than is the case with comparable stationary devices. In the volume images obtained during the operation extended body structures are cut off at the margins of the images. To improve the visualization, this restricted representation region is enlarged by use of the present method.

In the present example, during the repair of a pelvic fracture for which fixation with a plate is to occur, at the suitable time the previously created volume image of the larger object region A is made available. Registration can take place, for example, via marks that are placed on the patient during the volume imaging. By means of a matching of the marks that are detectable in the volume image with the marks remaining on the patient directly before the acquisition of the second 3D image data set or the implementation of the operation, for example by tapping of the marks on the patient with a navigation system instrument, such a matching can be achieved. In the process the navigation system also produces the reference to the imaging system of the C-arm device.

In the present example, first the volume image of the larger object region A is visualized on a screen. The physician now has the opportunity to shift, rotate and zoom out this representation three-dimensionally. This takes place using known interactive editing tools. The area around the fracture is now centered in this representation and zoomed out to the extent that the physician would now like to record it as an image with higher resolution and the current recording date. The virtual 3D coordinates of the smaller object region obtained in this connection are registered and used for setting the mobile C-arm device for the core region. Now with this mobile C-arm device on site in this setting with the highest resolution and optimum contrast, a volume image of the current position of the bone parts and, for example, partially inserted screw fixations, is created.

The resulting 3D core image then in the important step of the present method, is completed by the spatially further extending region of the 3D environment image. The environment image, i.e. the first 3D image data set of the larger object region A, generally must be repositioned for this purpose, i.e., rotated and shifted, as well as rescaled. This can take place with suitable hardware and software "on the fly" by means of suitable transformations or interpolations with the rendering hardware. Additionally it is possible, e.g., during the setting for the data acquisition of the object region B, to generate and save a transformed and new interpolated first 3D image data set, the 3D image data set then being synthesized with the second 3D image data set of the core region.

FIG. 2 shows an example of the generation of the synthesized 3D image data set from the first 3D image data set of the larger object region A and the second 3D image data set of the smaller object region B. In the volume image 1 of the larger object region A for this purpose the first image data, which reproduce the smaller object region B, are excised and replaced by the second image data of the second volume image 2, which in the present example is present with a higher resolution and an improved contrast. The synthesized 3D image data set is then visualized as volume image 3 on a monitor to the physician. The entire method, as explained in the present example, is shown in the flow chart of FIG. 1.

Of course the first volume image 1 and the second volume image 2 can also continue to be visualized separately. In addition it is advantageous to provide a shift function allowing shifting back and forth between the mapping of the core region from the preliminary examination and the current high resolution core image in the combined image representation. This method is also particularly informative when the core image has been acquired with completely different parameters, for example already positioned prosthetics or contrast media, or acquired a different modality e.g. ultrasound and/or endoscopy.

Also a semi-transparent superimposition of one or more currently-created core images with the image representation of the larger object region A can be additionally provided, with the superimposition being limited to the extent of the core image.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for displaying a volume image of an object region, comprising the steps of:
   providing at least one set of first 3D image data representing a larger object region of an object to a processor;
   acquiring at least one set of second 3D image data representing only a smaller object region of said object, said smaller object region being within said larger object region, by exposing said object to a data acquisition procedure in which only said second 3D image data are acquired, and providing said second 3D image data to said processor;
   in said processor, bringing said first 3D image data into registration with said second 3D image data;
   in said processor, generating a synthesized set of 3D image data from said first and second 3D image data in registration, by replacing a portion of said first 3D image data with said second 3D image data with identical scaling and alignment of said second 3D image data with a remainder of said first 3D image data; and
   visually displaying an image represented by said synthesized 3D image data.

2. A method as claimed in claim 1 wherein the step of generating said synthesized 3D image data set comprises adapting at least one of said first 3D image data and said second 3D image data to the other of said first 3D image data and said second 3D image data by an operation selected from the group consisting of image translation, image rotation, image enlargement and image reduction.

3. A method as claimed in claim 1 comprising acquiring said set of second 3D image data with a higher resolution than a resolution of said first set of 3D image data, and wherein the step of generating said synthesized 3D image data set comprises adapting said first 3D image data to said higher resolution by interpolation of said first 3D image data.

4. A method as claimed in claim 1 comprising acquiring said set of second 3D image data with a higher image contrast than a contrast of said set of first 3D image data.

5. A method as claimed in claim 1 comprising providing said set of first 3D image data as a set of first 3D tomographic image data, and comprising acquiring said set of second 3D image data with a tomographic imaging modality.

6. A method as claimed in claim 1 comprising, before acquiring said set of second 3D image data, generating and displaying an image of said larger object region from said set of first 3D image data and allowing manual user interaction, via a control unit that controls acquisition of said set of second 3D image data, to enter geometric data into the control unit, dependent on the display of the larger object region, and automatically controlling acquisition of said set of second 3D image data according to said geometrical data.

7. A method as claimed in claim 6 comprising allowing user interaction to selectively modify the image of the larger object region by an operation selected from the group consisting of image enlargement, image reduction, image rotation and image translation, to allow a data acquisition perspective to be selected for said set of second 3D image data, and allowing user entry of said selected imaging perspective into said control unit and controlling acquisition of said second set of 3D image data according to the selected imaging perspective.

8. A method as claimed in claim 1 comprising preprocessing said set of first 3D image data to retain therein only structures that are also of interest in said smaller object region represented by said set of second 3D image data.

9. A method as claimed in claim 1 comprising preprocessing said set of first 3D image data to highlight therein only structures that are also of interest in said smaller object region represented by said set of second 3D image data.

10. A method as claimed in claim 1 comprising automatically electronically determining a depth range within said set of first 3D image data containing structures also contained in said set of second 3D image data and wherein the step of generating said synthesized 3D image data set comprises replacing first 3D image data in said depth range with said set of second 3D image data.

11. A method as claimed in claim 10 comprising indexing each of said set of first 3D image data and said set of second 3D image data with respect to depth, and automatically electronically determining said depth range according to said indexing.

12. A method as claimed in claim 1 comprising allowing selective switching between display of said larger object region represented by said set of first 3D image data without replacement of said set of second 3D image data therein, and said image represented by said synthesized 3D image data set.

13. A method as claimed in claim 1 comprising allowing selective switching among different versions of an image of said smaller object region in an image of said larger object region, with said image of said smaller object region displayed with respectively different display characteristics.

14. A method as claimed in claim 13 comprising generating said different versions of said image of said smaller object region by superimposing said image of said smaller object region on said image of said larger object region with a display characteristic selected from the group consisting of a degree of transparency of said image of said smaller object region and a brightness of said image of said smaller object region.

15. A method as claimed in claim 1 wherein the step of providing at least one first set of 3D image data comprises providing a plurality of sets of first 3D image data that, in combination, represents said larger object region.

16. A method as claimed in claim 1 comprising providing said set of first 3D image data as a set of first 3D image data acquired using an imaging modality, and comprising acquiring said second set of 3D image data using the same imaging modality.

* * * * *